United States Patent
Woo et al.

(10) Patent No.: US 8,625,110 B2
(45) Date of Patent: Jan. 7, 2014

(54) METHODS OF INSPECTING STRUCTURES

(75) Inventors: Seouk-Hoon Woo, Hwaseong-si (KR); Jeong-Ho Yeo, Suwon-si (KR); Byeong-Ok Cho, Seoul (KR); Joo-On Park, Suwon-si (KR); Chang-Min Park, Hwaseong-si (KR); Won-Sun Kim, Suwon-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 700 days.

(21) Appl. No.: 12/662,079

(22) Filed: Mar. 30, 2010

(65) Prior Publication Data
US 2011/0007329 A1   Jan. 13, 2011

(30) Foreign Application Priority Data
Jul. 13, 2009  (KR) ..................... 10-2009-0063547

(51) Int. Cl.
*G01B 11/28* (2006.01)
(52) U.S. Cl.
USPC ............................ 356/630; 356/445; 356/612
(58) Field of Classification Search
USPC ........................................................ 356/630
See application file for complete search history.

(56) References Cited

U.S. PATENT DOCUMENTS 7,280,230 B2 * 10/2007 Shchegrov et al. ........... 356/630

FOREIGN PATENT DOCUMENTS

| JP | 2005-217161 | 8/2005 |
|---|---|---|
| JP | 2008-020451 | 1/2008 |
| KR | 10-2005-0080942 | 8/2005 |
| KR | 10-2008-0067285 | 7/2008 |

* cited by examiner

*Primary Examiner* — Tara S Pajoohi Gomez
(74) *Attorney, Agent, or Firm* — Harness, Dickey & Pierce, P.L.C.

(57) ABSTRACT

A method of inspecting a structure. The method includes preparing preliminary spectrums of reference diffraction intensities according to critical dimensions of reference structures, obtaining a linear spectrum from the preliminary spectrums in a set critical dimension range, radiating light to respective measurement structures formed on a substrate, measuring measurement diffraction intensities of the light diffracted by the measurement structures, and obtaining respective critical dimensions of the measurement structures from the measurement diffraction intensities using the linear spectrum.

13 Claims, 5 Drawing Sheets

METHODS OF INSPECTING STRUCTURES

CROSS-REFERENCE TO RELATED APPLICATION

This application claims priority under 35 U.S.C. §119 to Korean Patent Application No. 10-2009-0063547, filed on Jul. 13, 2009, in the Korean Intellectual Property Office (KIPO), the entire contents of which is incorporated herein by reference.

BACKGROUND

1. Field

Example embodiments relate to methods of inspecting structures, and more particularly, to methods of optically inspecting layer or pattern structures.

2. Description of Related Art

With an increase in the degree of integration of semiconductor devices the critical dimensions of structures may be reduced to tens of nanometers (nm). The critical dimensions of the structures may be measured by optical critical dimension (OCD) measurement. In OCD measurement, an approximate model may be formed and various intervening variables may be continuously changed to cancel differences in measurement between the model and structures to be inspected. In this process, a complex tool referred to as rigorous coupled wave analysis (RCWA) may be required. Conventional OCD measurement may be problematic in that a model must be approximately formed and it is difficult to cancel a difference in measurement between the model and measurement structures.

SUMMARY

Example embodiments of the inventive concepts provide methods of inspecting structures.

According to example embodiments of the inventive concepts, methods of inspecting a structure may include method may include preparing preliminary spectrums of reference diffraction intensities according to critical dimensions of reference structures, obtaining a linear spectrum from the preliminary spectrums in a set critical dimension range, radiating first light to respective measurement structures formed on a substrate; measuring measurement diffraction intensities of the first light diffracted by the measurement structures and obtaining respective critical dimensions of the measurement structures from the measurement diffraction intensities using the linear spectrum.

According to example embodiments of the inventive concepts, methods of inspecting a structure may include method may include preparing a plurality of preliminary spectrums each including a plurality of reference diffraction intensities, the reference diffraction intensities corresponding to critical dimensions of a plurality of reference structures, obtaining a linear spectrum based on the preliminary spectrums in a critical dimension range, radiating first light onto one or more measurement structures, measuring one or more measurement diffraction intensities of the first light diffracted by the measurement structures and obtaining critical dimensions of the measurement structures based on the measurement diffraction intensities and the linear spectrum.

According to example embodiments, the method may further include obtaining a correlation factor from the linear spectrum. The preliminary spectrums may be obtained by radiating second light to the reference structures whose critical dimensions are known and measuring reference diffraction intensities of the second light diffracted by the reference structures. The linear spectrum may be obtained in the set critical dimension range according to a wavelength and polarization mode of the second light. The wavelength and polarization mode of light having the obtained linear spectrum may be substantially the same as a wavelength and polarization mode of the first light.

According to example embodiments, when multiple linear spectrums are in the set critical dimension range, a linear spectrum having the steepest slope may be selected from among the multiple linear spectrums. The method may further include obtaining a distribution of the measurement diffraction intensities of the measurement structures and obtaining a distribution of the critical dimensions of the measurement structures. The measurement structures may include pattern structures.

According to example embodiments of the inventive concepts, methods of inspecting a structure may include preparing preliminary spectrums of reference diffraction intensities according to thicknesses of reference structures, obtaining a linear spectrum from the preliminary spectrums in a set thickness range, radiating light to measurement structures formed on a substrate, measuring measurement diffraction intensities of the light diffracted by the measurement structures; and obtaining respective thicknesses of the measurement structures from the measurement diffraction intensities using the linear spectrum.

According to example embodiments of the inventive concepts, methods of inspecting a structure may include preparing a plurality of preliminary spectrums each including a plurality of reference diffraction intensities, each of the plurality of spectrums corresponding to a thickness of a different plurality of reference structures, obtaining a linear spectrum based on the preliminary spectrums in a critical dimension range, radiating light onto one or more measurement structures, measuring one or more measurement diffraction intensities of the light diffracted by the measurement structures and obtaining thicknesses of the measurement structures based on the measurement diffraction intensities and the linear spectrum.

According to example embodiments, the measurement structures may include layer structures and pattern structures. The method may further include obtaining a distribution of the measurement diffraction intensities of the measurement structures; and obtaining a distribution of the thicknesses of the measurement structures.

According to example embodiments of the inventive concepts, methods of inspecting a structure may include generating a first data set including a first diffraction intensity and a second diffraction intensity, the first and second diffraction intensities corresponding to critical dimensions of first and second structures, respectively, on a substrate; generating a second data set based on at least part of the first data set in a critical dimension range, measuring a fourth diffraction intensity corresponding to a critical dimension of a fourth structure in the critical dimension range, and determining a magnitude of a physical property of the fourth structure based on the fourth diffraction intensity and the second data set.

BRIEF DESCRIPTION OF THE DRAWINGS

Example embodiments will be more clearly understood from the following brief description taken in conjunction with the accompanying drawings. FIGS. 1-7 represent non-limiting, example embodiments as described herein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Example embodiments of the inventive concepts will now be described more fully with reference to the accompanying drawings, in which example embodiments are shown. Example embodiments of the inventive concepts may, however, be embodied in many different forms and should not be construed as being limited to the embodiments set forth herein; rather, these embodiments are provided so that this disclosure will be thorough and complete, and will fully convey the concept of example embodiments to those of ordinary skill in the art. In the drawings, the thicknesses of layers and regions are exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments of the inventive concepts. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments of the inventive concepts may be described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments of the inventive concepts.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

It should also be noted that in some alternative implementations, the functions/acts noted may occur out of the order noted in the figures. For example, two figures shown in succession may in fact be executed substantially concurrently and/or may sometimes be executed in the reverse order, depending upon the functionality/acts involved.

Figure 1:
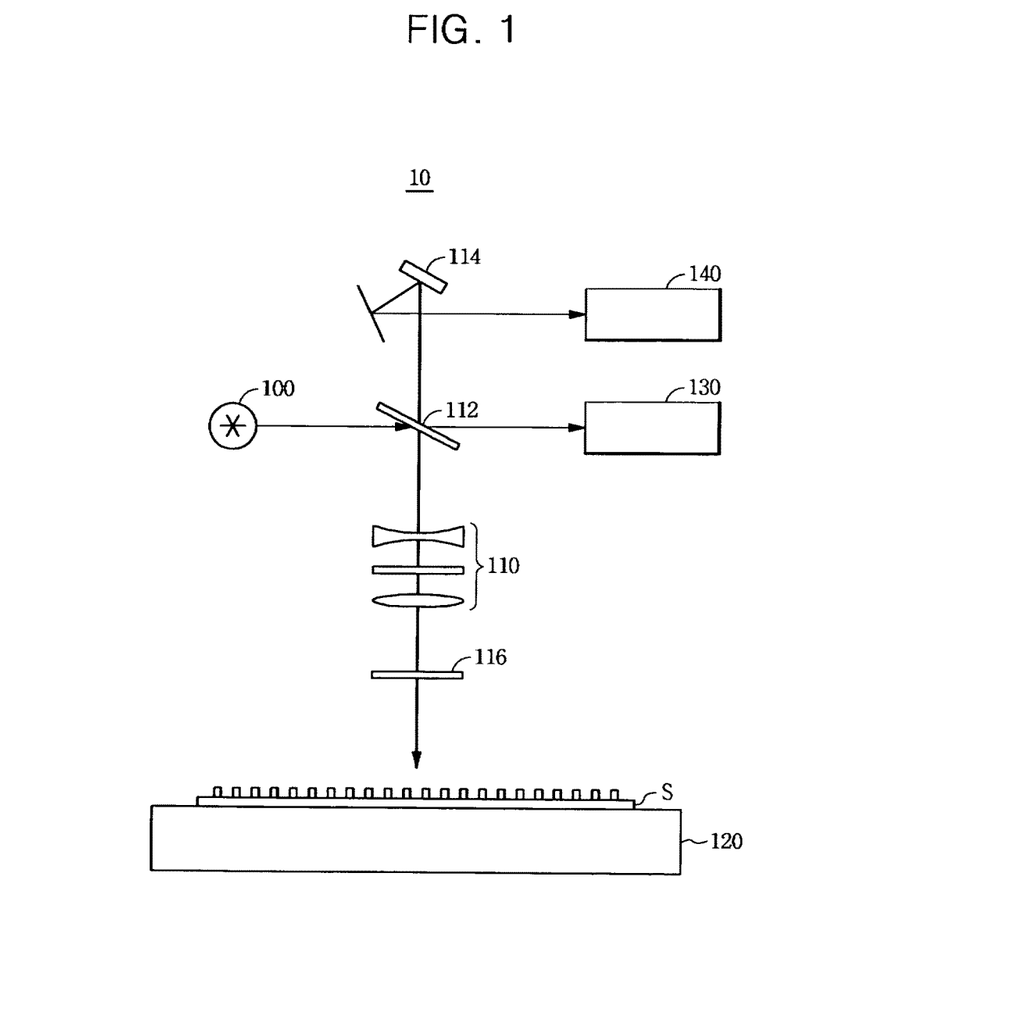
FIG. 1 is a schematic illustrating an optical critical dimension (OCD) measurement apparatus according to example embodiments of the inventive concepts.

FIG. 1 is a schematic illustrating an optical critical dimension (OCD) measurement apparatus 10 according to example embodiments of the inventive concepts. The OCD measurement apparatus 10 may measure the critical dimensions, thicknesses, and the like, of structures in a nondestructive method using light of a specific wavelength range. The OCD measurement apparatus 10 may be used, for example, to monitor process variation after preventive maintenance (PM). In a lithography process, the OCD measurement apparatus 10 may measure the critical dimensions and thicknesses of structures to be formed by After-Development Inspection (ADI) or After-Etching Inspection (AEI).

Techniques used in the OCD measurement apparatus 10 may be classified, for example, into scatterometry, ellipsometry, normal incidence reflectance spectrometry, normal incidence ellipsometry, and the like. Scatterometry may include, for example, two techniques. One technique may be spectroscopic scatterometry that uses a broad-band light source and measures properties of light scattered at a fixed angle. The light scattered at the fixed angle may be normally or diagonally incident on the surface of a substrate. The other technique may be angle-resolved scatterometry. The angle-resolved scatterometry may measure properties of light scattered at a wavelength fixed as a function of an incident angle using a laser, which may be a single-wavelength and/or narrow-band light source.

The OCD measurement apparatus 10 will now be described with reference to FIG. 1. Referring to FIG. 1, the OCD measurement apparatus 10 may include a light source 100, a projector 110, a substrate support 120, a first detector 130, and a second detector 140. The light source 100 may generate light. The light generated from the light source 100 may be normally or diagonally incident on the upper surface of a substrate S. The light generated from the light source 100 may have a single wavelength or multiple wavelengths. Light incident on the substrate S may have, for example, a single wavelength. The wavelength of the light incident on the substrate S may vary according to time or a purpose of an operator.

According to example embodiments, the light source 100 may be a broad-band wavelength light source. The broad-band wavelength light source may generate light of multiple wavelengths and may selectively generate light of a desired wavelength. The broad-band wavelength light source may generate light of a specific wavelength, for example, according to time or a purpose of an operator. According to example embodiments of the inventive concepts, the light source 100 may be a tunable laser. The tunable laser may generate light of multiple wavelengths and may selectively generate a laser beam of a desired wavelength. The tunable laser may generate light of a specific wavelength, for example, according to time or a purpose of an operator.

According to example embodiments of the inventive concepts, the light source 100 may generate light of multiple wavelengths. The light source 100 generating light of multiple wavelengths may be, for example, an incandescent bulb and the OCD measurement apparatus 10 may include a filter. The filter may select light of a desired wavelength from the light of multiple wavelengths. For example, the filter may be disposed adjacent to the light source 100 between the substrate support 120 and the light source 100.

The light source 100 may be included in the OCD measurement apparatus 10 or spaced apart from the OCD measurement apparatus 10. When the light source 100 is spaced apart from the OCD measurement apparatus 10, the OCD measurement apparatus 10 may further include a light guide so that light generated from the light source 100 can be guided to the substrate S.

The first detector 130 may detect properties of light generated from the light source 100. For example, by measuring the wavelength and polarization mode of light generated from the light source 100, the first detector 130 may detect properties of the light. The first detector 130 may detect the properties of light from part of the light generated from the light source 100. For example, a beam splitter 112 may redirect a portion of the light. A part of the light generated from the light source 100 may be radiated to the substrate S, a part may be radiated to the first detector 130, and/or a part may be radiated to a blazed grating 114. The blazed grating 114 may include a series of grooves and may change the incident angle of the light generated from the light source 100 using the grooves. The generated light may be directly radiated to the substrate S, the first detector 130, the blazed grating 114 and/or radiated by a plurality of reflectors. Although not illustrated in the drawing, the first detector 130 may be connected with the second detector 140 and transfer light properties to the second detector 140.

The projector 110 may function to guide and radiate light generated from the light source 100 to the substrate S disposed on the substrate support 120. The projector 110 may include a lens array including a condensing lens and various types of reflecting mirrors. The projector 110 may radiate light generated from the light source 100 to be normally incident on the upper surface of the substrate S. The projector 110 may radiate light generated from the light source 100 to be incident on the upper surface of the substrate S at a predetermined angle $\ominus$. Light incident on the substrate S may be radiated onto a measurement region of the substrate S or the entire region of the substrate S. When the incident light is radiated onto the measurement region of the substrate S, a process of scanning the entire substrate S may be additionally performed.

A polarizing plate 116 may be between the light source 100 and the substrate support 120. For example, the polarizing plate 116 may be adjacent to the substrate support 120. Light generated from the light source 100 may have a random polarization, but may be specifically polarized by the polarizing plate 116. The travel mode of the polarized light may include a transverse electric field (TE) mode and a transverse magnetic field (TM) mode. Properties of light radiated to the substrate S may be important factors for obtaining characteristics of structures. The properties of the light may be, for example, the wavelength and/or polarization mode of the light. Characteristics of structures may be, for example, the critical dimensions and/or thicknesses of the structures.

The substrate support 120 may support the substrate S. The substrate support 120 may be disposed to face the light source 100. For example, the light source 100 may be disposed in a direction perpendicular or diagonal to the upper surface of the substrate support 120. The substrate support 120 may include a body, multiple lift fingers, a fixing unit, and/or a driving unit (not shown). The multiple lift fingers may move up or down from the inside of the body to the upper surface of the body. The multiple lift fingers may move up and/or down to load and/or unload the substrate S on or from the body. The multiple lift fingers may be spaced apart from each other, for example, by the same distance. There may be, for example, three lift fingers.

The fixing unit may function to fix the substrate S on the body of the substrate support 120 while structures formed on the substrate S are measured using the OCD measurement apparatus 10. For example, the fixing unit may include a vacuum pump and vacuum lines. Multiple vacuum holes leading to the vacuum lines may be formed in the body and connect the vacuum holes with the vacuum pump. The fixing unit may fix the lower surface of the substrate S on the upper surface of the body using vacuum. The fixing unit may include an electrostatic generator. The fixing unit may fix the lower surface of the substrate S on the upper surface of the body using static electricity. The fixing unit may use vacuum and/or static electricity, but the type or fixing method of the fixing unit is not limited herein.

The driving unit may be electrically connected with the body and may move the substrate S, fixed and supported on the body, in X-axis, Y-axis and Z-axis directions. The driving unit may be electrically connected with the lift fingers and/or move the lift fingers up and/or down. By the driving unit, the substrate S may be moved to a desired position and the surface of the substrate S may also be scanned. The driving unit may be electrically connected with a control unit and, for example, control the position of the substrate S and/or movement of the lift fingers. The control unit may, for example, control the movement path, movement speed, and/or movement time of the substrate S. The control unit may control, for example, the movement direction of the lift fingers to load and/or unload the substrate S.

The substrate S may include a cell area and a peripheral area. Measurement structures may be formed in the cell area. Reference structures may be formed in the peripheral area, and/or on a substrate different from the substrate S on which the measurement structures are formed. The substrate S may be, for example, a silicon (Si) substrate, a germanium (Ge) substrate, or a substrate including Si and Ge. The substrate S may include a chromium (Cr) layer. A photoresist pattern may be on the substrate S including the Cr layer.

The structures may include layer structures and pattern structures. The measurement structures may have unknown critical dimensions and/or thicknesses. Although a process may be performed for a desired critical dimension and/or thickness, some of the completed measurement structures may have a critical dimension and/or thickness different from the desired critical dimension and/or thickness. For example, when the critical dimension and/or thickness of the completed measurement structure are different from the desired critical dimension and/or thickness by more than, for example, about ±10%, the measurement structures may be determined as defective. When the critical dimension and thickness of the completed measurement structure are different from the desired critical dimension and/or thickness by, for example, about ±10% or less, the measurement structures may not be determined as defective. Ranges within about ±10% of the desired critical dimension and/or thickness for the completed measurement structures may be referred to as a set critical dimension range and/or set thickness range.

For example, when the desired critical dimension of the measurement structures is about 35 nm, the set critical dimension range may be from about 30 nm to 40 nm. The set critical dimension range may include the desired critical dimension, and/or the set thickness range may include the desired thickness. When the measurement structures include pattern structures the pattern structures may constitute an array and may not be isolated. The critical dimension may include a space critical dimension and/or a bar critical dimension. The space critical dimension may be a distance between adjacent pattern structures among the pattern structures and the bar critical dimension may be the width of the pattern structures. When the space critical dimension is substantially the same as the bar critical dimension, the pattern structures may be referred to as line and space pattern structures.

For example, when the measurement structures are pattern structures, the space critical dimension may be substantially the same as the bar critical dimension. The measurement structures may be line and space pattern structures. The space critical dimension may be substantially different from the bar critical dimension. A ratio of the space critical dimension of the pattern structures (e.g., a ratio of the measurement structures to the bar critical dimension) is not limited. The reference structures may be used as a reference for measuring the critical dimension and/or thickness of the measurement structures. Because the critical dimension and/or thickness of the reference structures may be already known values, the critical dimension and/or thickness of the measurement structures may be obtained by measuring the diffraction intensities of the reference structures according to the critical dimension and/or thickness of the reference structures.

The reference structures may be on substantially the same substrate S as the measurement structures and/or a different substrate S than the measurement structures. According to example embodiments of the inventive concepts, the reference structures may be photoresist pattern structures. A photoresist layer may be on the substrate S. When the reference structures are formed on the same substrate S as the measurement structures, the photoresist layer may be formed in the peripheral area or cell area of the substrate S. The substrate S on which the photoresist layer is formed may be moved to a lithographic apparatus.

The lithographic apparatus may include a source, a support that supports the substrate S, and/or a reticle disposed between the source and the support. The reticle may include a pattern having a set critical dimension. The set critical dimension of the reticle may be referred to as a reticle critical dimension. Light may be generated from the source, passed through the reticle and radiated to the photoresist layer, thereby performing a lithography process. During the lithography process, the intensity of the source may be adjusted, so that a photoresist pattern may have a critical dimension substantially different from the reticle critical dimension.

A distance between the support and the source may be adjusted so that a photoresist pattern may have a critical dimension substantially different from the reticle critical dimension. The critical dimension of the photoresist pattern may be substantially smaller or larger than the reticle critical dimension. The critical dimension of the photoresist pattern may be in the set critical dimension range. Through a development process and baking process, photoresist patterns may be formed from the exposed photoresist layer. The critical dimension and/or thickness of the photoresist patterns may be measured in a method using, for example, a scanning electron microscope (SEM).

According to example embodiments of the inventive concepts, the reference structures may be an oxide, a nitride, a carbide, and/or a conductive material. A reference structure layer including an oxide, a nitride, a carbide, and/or a conductive material may be on the substrate S. The reference structure layer may have a multi-layer structure including the oxide, nitride, carbide, and/or conductive material. A photoresist layer may be on the reference structure layer. By performing lithography, development and baking processes on the photoresist layer, photoresist patterns may be formed on the reference structure layer. During the lithography process, the intensity of the source or a distance between the support and the source may be adjusted, so that the photoresist patterns may have a critical dimension substantially different from the reticle critical dimension. The critical dimensions of the photoresist patterns may be in the set critical dimension range.

The reference structures may be formed by etching the reference structure layer using the photoresist patterns as an etch mask. For example, the reference structures may have substantially the same critical dimension as the photoresist patterns. The reference structures may have, for example, substantially different critical dimension than the photoresist patterns. The critical dimensions of the reference structures may be in the set critical dimension range. After the reference structures are formed, the photoresist patterns may be removed. The photoresist patterns may be removed, for example, through an ashing process and/or a chemical cleaning process. The critical dimension and/or thickness of the reference structures may be measured according to a method using, for example, a SEM.

The second detector 140 may detect the intensity of light that is radiated onto the substrate S and diffracted by the reference structures and/or the measurement structures. The intensity of light diffracted by the reference structures may be referred to as a reference diffraction intensity and the intensity of light diffracted by the measurement structures may be referred to as a measurement diffraction intensity. The second detector 140 may measure reference diffraction intensities and obtain preliminary spectrums of the reference diffraction intensities according to the critical dimension of the reference structures. The second detector 140 may obtain preliminary spectrums of the reference diffraction intensities according to the thickness of the reference structures. The obtained preliminary spectrums may vary according to the wavelength and polarization mode of light radiated onto the reference structures.

From the preliminary spectrums, linear spectrums may be obtained in the set critical dimension range. Linear spectrums may be obtained in the set thickness range. The second detector 140 may measure measurement diffraction intensities and calculate the critical dimension and/or thickness of the measurement structures from the measurement diffraction intensities using the linear spectrums.

Figure 2:
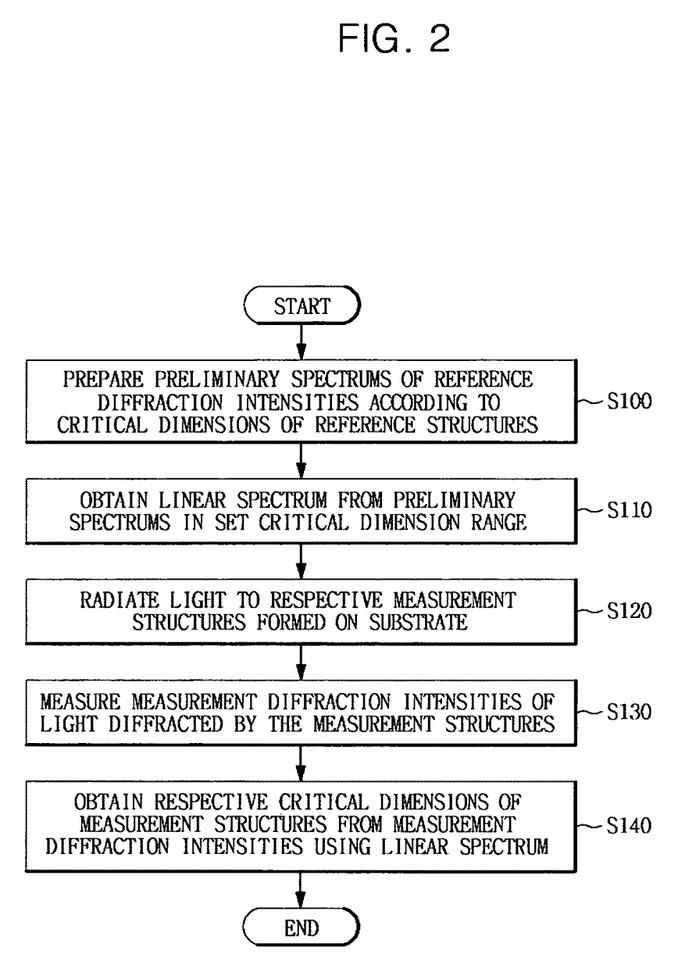
FIG. 2 is a flowchart illustrating methods of inspecting structures according to example embodiments of the inventive concepts.
Figure 3:
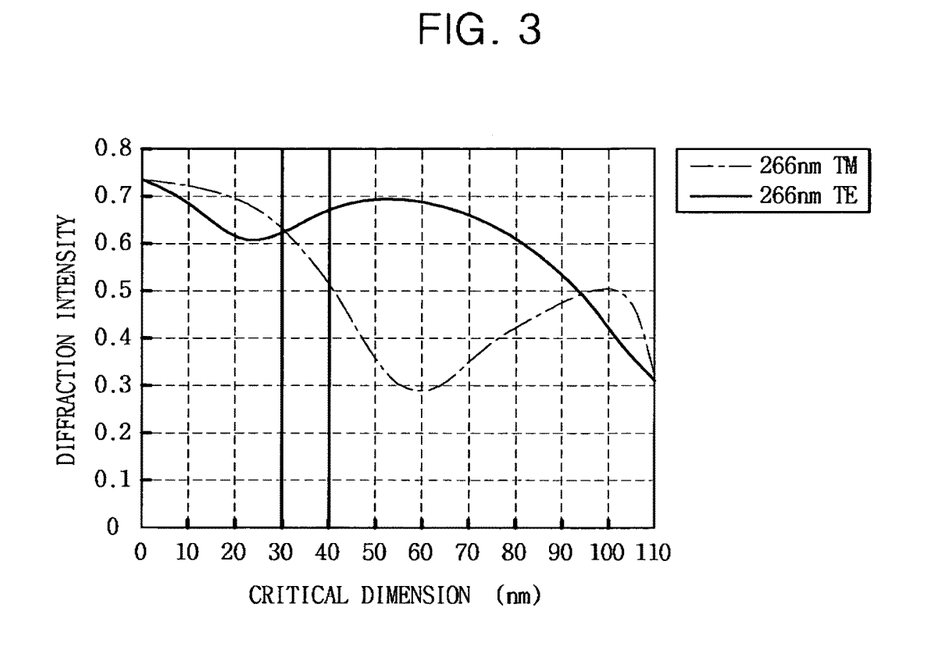
FIG. 3 is a graph of Diffraction Intensity as a function of Critical Dimension (nm) illustrating preliminary spectrums of reference diffraction intensities corresponding to critical dimensions of reference structures according to example embodiments of the inventive concepts.
Figure 4:
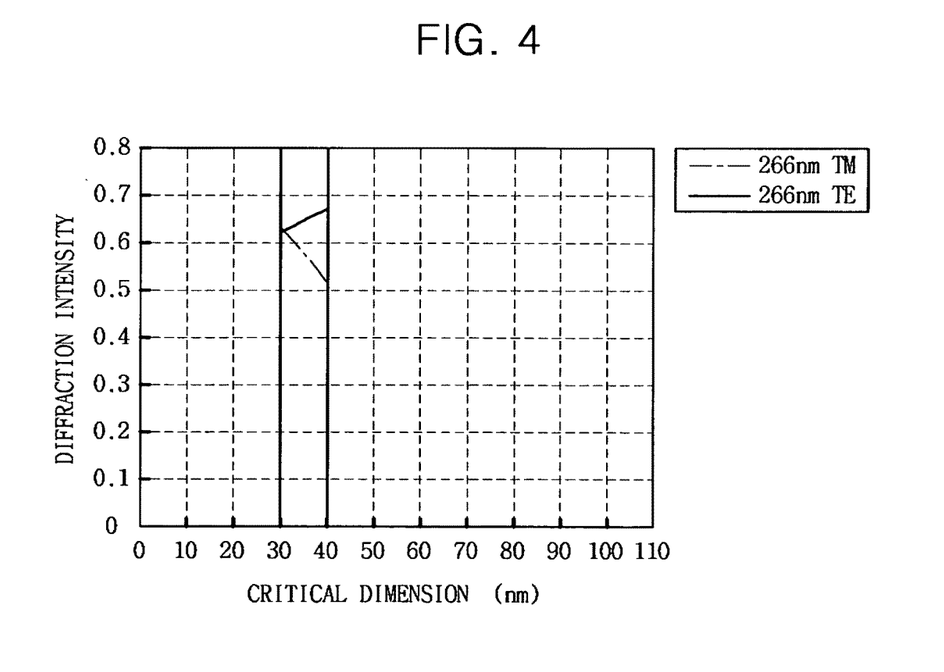
FIG. 4 is a graph of Diffraction Intensity as a function of Critical Dimension (nm) illustrating linear spectrums selected from the preliminary spectrums shown in FIG. 3 in a set critical dimension range.
Figure 5:
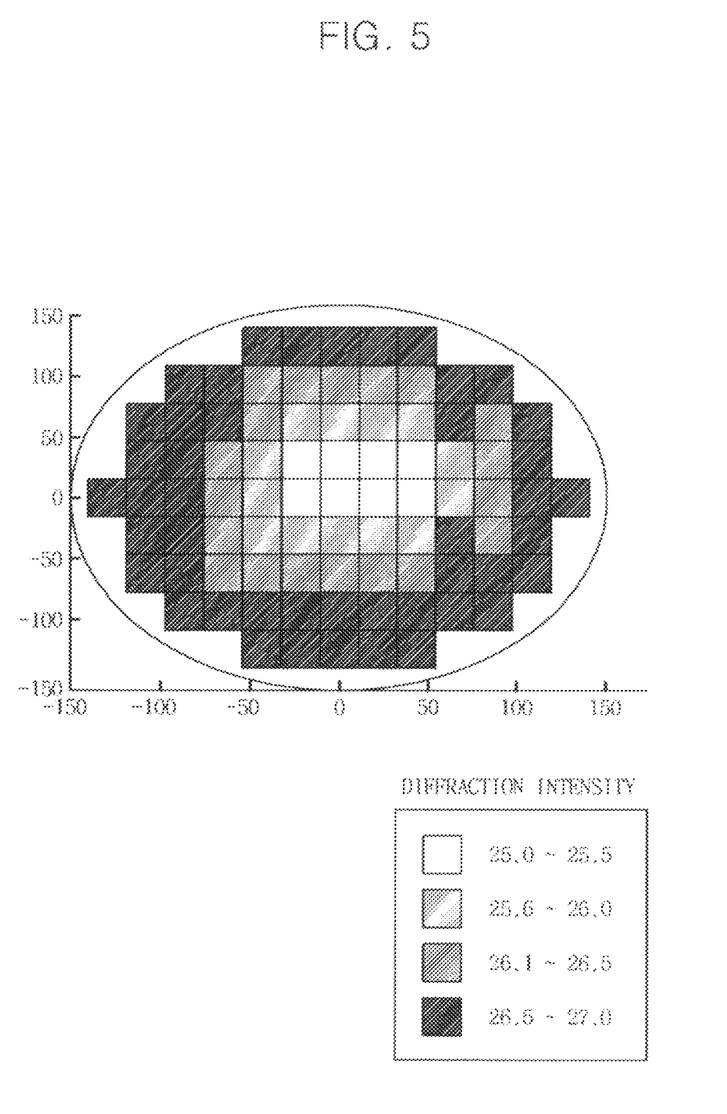
FIG. 5 is a wafer map illustrating a distribution of measurement diffraction intensities of measurement structures on a substrate.

FIG. 2 is a flowchart illustrating methods of inspecting structures according to example embodiments of the inventive concepts. FIG. 3 is a graph of Diffraction Intensity as a function of Critical Dimension (nm) illustrating preliminary spectrums of reference diffraction intensities according to the critical dimensions of reference structures, each spectrum corresponding to a polarization and wavelength of light. FIG. 4 is a graph of Diffraction Intensity as a function of Critical Dimension (nm) illustrating linear spectrums selected from the preliminary spectrums shown in FIG. 3 in a set critical dimension range. FIG. 5 is a wafer map illustrating a distribution of measurement diffraction intensities of measurement structures on a substrate. Among characteristics of structures, the critical dimension may be described below as an example and substantially the same description may be applied to the thickness of the structures.

Referring to FIG. 2, preliminary spectrums of diffraction intensities according to the critical dimensions of reference structures may be prepared according to S100. Reference structures may be formed on a substrate. For example, the reference structures may be formed on the substrate and/or measurement structures may be formed on the substrate. The reference structures may be formed in the peripheral area of the substrate and the measurement structures may be formed in the cell area. According to example embodiments of the inventive concepts, the reference structures may be photoresist patterns. The reference structures may be oxide structures, nitride structures, and/or metal structures. The reference structures may have substantially different critical dimensions and/or thicknesses, which may be known values.

Light may be radiated onto the reference structures. The first detector 130 may detect properties of the radiated light. The properties of the radiated light may be, for example, the wavelength and/or polarization mode of the light. The properties of the light may be required in order to obtain a linear spectrum. The radiated light may be diffracted by the reference structures and the intensity of light diffracted by the reference structures may be detected by the second detector 140. The intensities of light diffracted by the reference structures may be referred to as reference diffraction intensities. The diffracted light may have various diffraction orders. The diffracted light may include a zeroth order to $\pm N^{th}$ orders (N is an integer). The diffracted light may be mostly zeroth order. The zeroth order diffraction light may denote light whose incident angle and reflection angle are substantially the same.

Preliminary spectrums of the reference diffraction intensities according to the critical dimensions of the reference structures may be obtained according to S110. The preliminary spectrums may vary according to the properties of the radiated light, for example, the wavelength and/or polarization mode of the radiated light. The preliminary spectrums may have linear sections over a range and may tend to have low and/or decreased reference diffraction intensities as the wavelength increases.

In the set critical dimension range, a linear spectrum may be obtained from the preliminary spectrums. The set critical dimension range may correspond to ±10% the desired critical dimension of the measurement structures. Referring to FIGS. 3 and 4, for example, when the critical dimension of the measurement structures is about 35 nm, the set critical dimension range may be from about 30 nm to 40 nm. Measurement structures having a critical dimension exceeding the set critical dimension range may be determined as defective and may not have a measurement diffraction intensity value.

The method of obtaining a linear spectrum from the preliminary spectrums may be a linear fitting method, for example, linear regression analysis. When multiple linear spectrums are in the set critical dimension range a linear spectrum having the steepest slope may be selected from among the multiple linear spectrums. A linear spectrum having the largest ratio of an increase in the reference diffraction intensity of the reference structures (increase in the Y-axis) to an increase in the critical dimension of the reference structures (increase in the X-axis) may be selected. A preliminary spectrum including the selected linear spectrum may be checked. The wavelength and polarization mode of the radiated light radiated when the preliminary spectrum is obtained may be checked. The wavelength and polarization mode of the light may be referred to as a reference wavelength and reference polarization mode. The reference wavelength and reference polarization mode may be important factors for determining properties of light radiated to the measurement structures.

A correlation factor may be obtained from the selected linear spectrum. The linear spectrum may have an equation in the form of "Y=aX+b." Y may denote the intensity of light, X may denote a critical dimension, and a and b may be correlation factors. The values of a and b may be obtained from the linear spectrum. The equation in which the correlation factors are determined may be used to determine the critical dimensions of the measurement structures.

A substrate on which the measurement structures are formed may be prepared. For example, the measurement structures may be formed in a cell area of the substrate. The measurement structures may have unknown critical dimensions and/or thicknesses. Although a process may be performed for a desired critical dimension and thickness, some of the completed measurement structures may have a critical dimension and thickness different from the desired critical dimension and thickness.

When the critical dimension of the completed measurement structure is different from the desired critical dimension by more than about ±10%, the measurement structure may be determined as defective. On the other hand, when the critical dimension of the completed measurement structure is different from the desired critical dimension by about ±10% or less, the measurement structure may not be determined as defective. In this case, a set critical dimension range may be between about ±10% the desired critical dimension for the completed measurement structures. One having ordinary skill in the art understands that a set critical dimension range need may be set according to, for example, requirements of a semiconductor process.

When the measurement structures include pattern structures, the pattern structures may constitute an array and may not be isolated. As an example, when the measurement structures are pattern structures, the space critical dimension may be substantially the same as the bar critical dimension. The measurement structures may be line and space pattern structures. The space critical dimension may be substantially different from the bar critical dimension. A ratio of the space critical dimension of the pattern structures included in the measurement structures to the bar critical dimension is not limited.

Light may be radiated onto the measurement structures according to S120. The wavelength and polarization mode of the light radiated onto the measurement structures may substantially the same as the reference wavelength and/or reference polarization mode. The intensity (measurement diffraction intensity) of light diffracted by the measurement structure may be measured by the second detector 140 according to S130. By scanning the substrate, it may be possible to measure, for example, all of the measurement diffraction intensities of the measurement structures formed on the substrate.

The process distribution of the measurement structures may be measured using the measurement diffraction intensities. The respective measurement diffraction intensities may be illustrated to correspond to positions on the substrate at which the measurement structures are formed. The positions on the substrate may be illustrated as different brightnesses and colors according to the measurement diffraction intensity values. Referring to FIG. 5, the substrate may be divided into multiple regions which have different brightnesses according to the measurement diffraction intensities. The regions may become brighter from the edge of the substrate to the center. The brighter a region, the higher the measurement diffraction intensity of the region may be. The distribution of the measurement diffraction intensities of the measurement structures formed on the substrate may be visually checked with reference to a wafer map (e.g., the wafer map of FIG. 5). From the distribution of the measurement diffraction intensities, it may be possible to infer the critical dimension distribution of the measurement structures.

According to example embodiments of the inventive concepts, the critical dimensions of the measurement structures may be substantially the same and/or brightnesses and/or colors shown in the wafer map may be substantially the same. From the distribution of the measurement diffraction intensities, it may be possible to infer the critical dimension distribution of the measurement structures. From the fact that brightnesses or colors shown in the substrate are substantially the same, it may be possible to infer that a difference value between the critical dimensions of the measurement structures formed on the substrate is about zero.

By inserting the respective measurement diffraction intensity values into the linear spectrum equation, the respective critical dimensions of the measurement structures may be obtained according to S140. The critical dimensions of the measurement structures may be in the set critical dimension range. When the critical dimensions of the measurement structures exceed the set critical dimension range, the critical dimensions of the measurement structures may not be obtained.

The critical dimension distribution of the measurement structures may be obtained using the obtained critical dimensions. By illustrating the critical dimension distribution of the measurement structures on the wafer map in the same method as described for the measurement diffraction intensity distribution, the critical dimensions of the measurement structures may be readily, visually checked.

According to example embodiments including inspecting a structure, the conventional step of forming an approximate model and the conventional fitting step of removing a difference between the model and structures to be actually measured may not be performed. It may be possible to readily and effectively inspect structures. Using the distribution of measurement diffraction intensities obtained from the measurement structures or the critical dimension distribution of the measurement structures, it may be possible to readily, visually check characteristics of the measurement structures.

Figure 6:
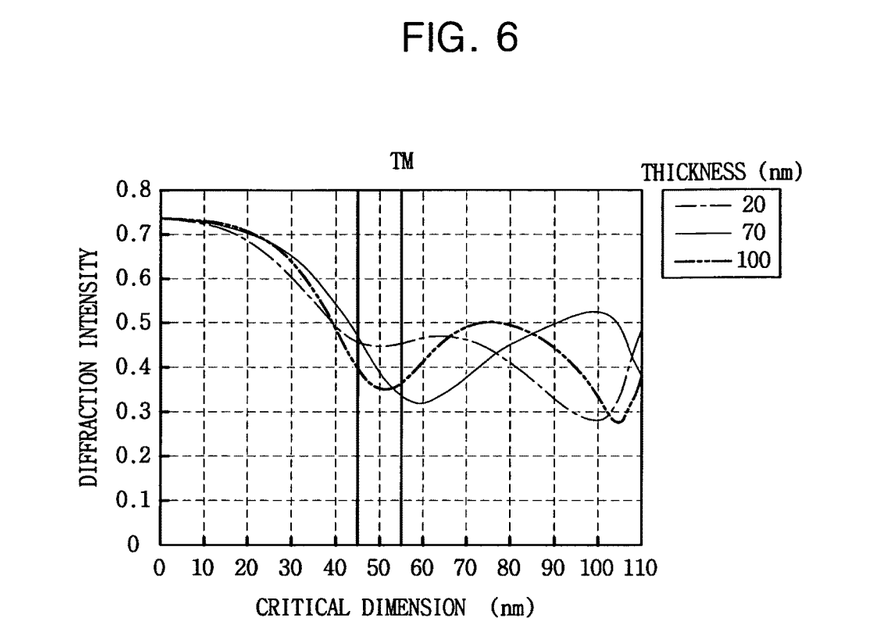
FIGS. 6 and 7 are graphs of Diffraction Intensity as a function of Critical Dimension (nm) illustrating preliminary spectrums of diffraction intensities corresponding to critical dimensions and thicknesses according to example embodiments of the inventive concepts.
Figure 7:
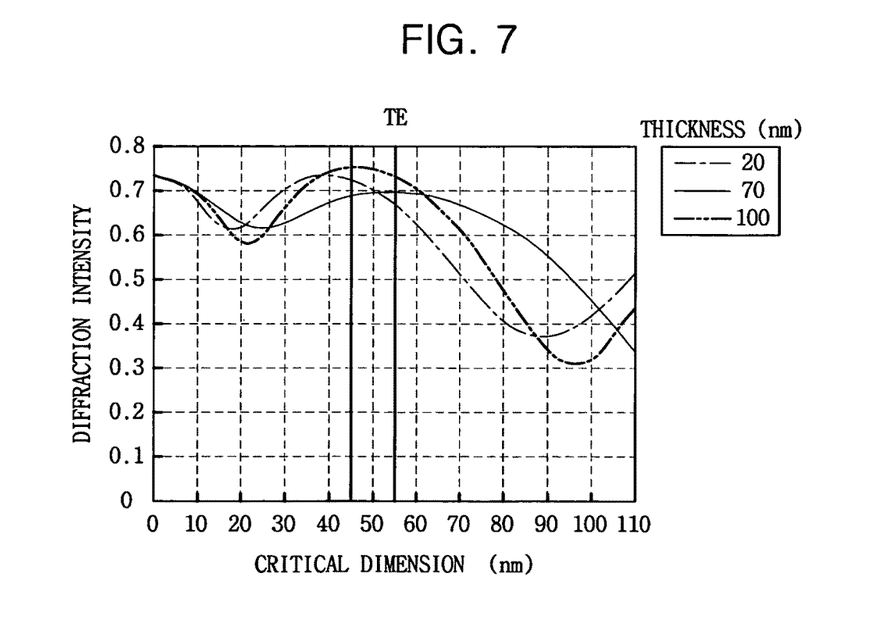

FIGS. 6 and 7 are graphs of Diffraction Intensity as a function of Critical Dimension (nm) illustrating preliminary spectrums of diffraction intensities according to critical dimensions for 3 thicknesses, obtained using a method of inspecting a structure according to example embodiments of the inventive concepts. FIG. 6 may illustrate preliminary spectrums for TM polarized light and FIG. 7 may illustrate preliminary spectrums for TE polarized light. The preliminary spectrums of FIGS. 6 and 7 may be obtained using pattern structures as reference structures. The reference structures may have multi-layer structures in which a lower pattern is formed of, for example, silicon nitride (SiN) and an upper pattern is formed of, for example, silicon oxide ($SiO_2$). The lower pattern may have a thickness of about 145 nm. The reference structures may be line and space pattern structures whose space critical dimensions are substantially the same as the bar critical dimensions.

The preliminary spectrums shown in FIGS. 6 and 7 may be obtained using light having a wavelength of about 266 nm. The preliminary spectrums shown in FIG. 6 may be obtained using light in the TM polarization mode and the preliminary spectrums shown in FIG. 7 may be obtained using light in the TE polarization mode. FIGS. 6 and 7 may be different in polarization mode only. Referring to FIGS. 6 and 7, when the upper pattern has a critical dimension range from about 45 nm to 55 nm preliminary spectrums corresponding to the upper pattern thicknesses of about 20 nm, 70 nm and 100 nm may be examined. In FIG. 6, spectrums corresponding to thicknesses of about 20 nm and about 100 nm may not be linear and may not be selected as a linear spectrum.

Referring to FIG. 7, spectrums corresponding to the thicknesses of about 100 nm and about 20 nm may be selected as linear spectrums. The slope of the spectrum corresponding to the thickness of about 70 nm may have a small absolute value and it may be difficult to select the spectrum corresponding to a thickness of about 70 nm as a linear spectrum. When the thickness of a measurement structure is about 20 nm or about 100 nm, light having a wavelength of about 266 nm and the TE mode may be selected to perform the method of inspecting a structure.

According to example embodiments of the inventive concepts, a thickness and/or critical dimension of a measurement structure may be obtained with reference to linear spectrums generated from reference structures. For example, a critical dimension of a measurement structure may be obtained by measuring a thickness of the measurement structure prior to patterning. For example, a thickness may be determined by measuring diffraction intensities of the unpatterned measurement structures and comparing them to diffraction intensities of a reference structure in which a space has a dimension of 0. For example, diffraction intensities of the unpatterned measurement structures may correspond to a critical dimension in FIGS. 6 and 7 of about 110 nm. A measurement structure may be patterned and one or more diffraction intensities of the measurement structure measured. A critical dimension of the measurement structure may be determined from the measured diffraction intensities of the patterned measurement structure with reference to one or more linear spectrums.

Example embodiments are not limited to measuring a thickness of an unpatterned structure and one having ordinary skill in the art will understand that, for example, a thickness of a measurement structure may be determined from a patterned measurement structure having a known and/or determined critical dimension. Further, one having ordinary skill in the art will understand that both a thickness and a critical dimension of a measurement structure may be determined with reference to, for example, one or more linear spectrums without first determining either the thickness or critical dimension of the measurement structure.

A method of measuring the critical dimensions and/or thicknesses of measurement structures based on measurement diffraction intensities using a linear spectrum obtained from preliminary spectrums may be provided according to example embodiments of the inventive concepts. Conventional steps of forming an approximate model and canceling a difference in measurement between the model and measurement structures may be eliminated and it may be possible to readily and rapidly measure the critical dimensions and thicknesses of structures.

The foregoing is illustrative of example embodiments of the inventive concepts and is not to be construed as limiting thereof. For example, example embodiments may be applied to a measurement method for monitoring process variation in semiconductor equipment. While example embodiments of the inventive concepts have been particularly shown and described, it will be understood by one of ordinary skill in the art that variations in form and detail may be made therein without departing from the spirit and scope of the claims.

What is claimed is:

1. A method of inspecting a structure, comprising:
preparing a plurality of preliminary spectrums each including a plurality of reference diffraction intensities, the reference diffraction intensities corresponding to critical dimensions of a plurality of reference structures;
obtaining a linear spectrum based on the preliminary spectrums, the linear spectrum being a linear approximation for only segments of the preliminary spectrums in a desired critical dimension range of one or more measurement structures;
radiating first light onto the one or more measurement structures;
measuring one or more measurement diffraction intensities of the first light diffracted by the measurement structures; and
obtaining critical dimensions of the measurement structures based on the measurement diffraction intensities and the linear spectrum.

2. The method of claim 1, further comprising obtaining a correlation factor based on the linear spectrum.

3. The method of claim 1, further comprising:
radiating second light onto the reference structures, the reference structures having known critical dimensions; and
measuring the reference diffraction intensities of the second light diffracted by the plurality of reference structures,
wherein the linear spectrum corresponds to one of a plurality of wavelength and polarization mode pairs of the second light.

4. The method of claim 3, wherein each of the preliminary spectrums corresponds to a different one of the wavelength and polarization mode pairs of the second light.

5. The method of claim 3, wherein the wavelength and polarization mode of the second light corresponding to the linear spectrum is substantially the same as a wavelength and polarization mode of the first light.

6. The method of claim 1, wherein the linear spectrum has a steepest slope of a plurality of linear spectrums in the desired critical dimension range.

7. The method of claim 1, further comprising:
obtaining a distribution of the measurement diffraction intensities of the first light diffracted by the measurement structures; and
obtaining a distribution of the critical dimensions of the measurement structures.

8. The method of claim 1, wherein the measurement structures include pattern structures.

9. The method of claim 1, wherein the desired critical dimension range is a set critical dimension range.

10. A method of inspecting a structure, comprising:
preparing a plurality of preliminary spectrums each including a plurality of reference diffraction intensities, each of the plurality of spectrums corresponding to a thickness of a different plurality of reference structures;
obtaining a linear spectrum based on the preliminary spectrums in a critical dimension range;
obtaining a linear spectrum equation in which at least one correlation factor is determined from the linear spectrum;
radiating light onto one or more measurement structures;
measuring one or more measurement diffraction intensities of the light diffracted by the measurement structures; and
obtaining thicknesses of the measurement structures by inserting values of the measurement diffraction intensities into the linear spectrum equation.

11. The method of claim 10, wherein the measurement structures include layer structures and pattern structures.

12. The method of claim 10, further comprising:
obtaining a distribution of the measurement diffraction intensities of the light diffracted by the measurement structures; and
obtaining a distribution of the thicknesses of the measurement structures.

13. The method of claim 12, further comprising:
generating a wafer map by dividing an area including the measurement structures into one or more regions corresponding to positions on a substrate at which the measurement structures are located, assigning the regions at least one of a brightness and color based on the measurement diffraction intensities corresponding to the measurement structures located in the regions, and generating a graphical representation of the substrate and the regions.

* * * * *